United States Patent
Hillis et al.

(10) Patent No.: US 9,778,395 B2
(45) Date of Patent: Oct. 3, 2017

(54) SECURITY SCANNING DEVICE

(71) Applicant: Elwha LLC, Bellevue, WA (US)

(72) Inventors: W. Daniel Hillis, Cambridge, MA (US); Roderick A. Hyde, Redmond, WA (US); Jordin T. Kare, San Jose, CA (US); Eric C. Leuthardt, St Louis, MO (US); Lowell L. Wood, Jr., Bellevue, WA (US)

(73) Assignee: Elwha LLC

( * ) Notice: Subject to any disclaimer, the term of this patent is extended or adjusted under 35 U.S.C. 154(b) by 0 days.

(21) Appl. No.: 15/399,505

(22) Filed: Jan. 5, 2017

(65) Prior Publication Data

US 2017/0115430 A1    Apr. 27, 2017

Related U.S. Application Data

(63) Continuation of application No. 14/675,427, filed on Mar. 31, 2015, now Pat. No. 9,551,673, which is a continuation of application No. 13/895,596, filed on May 16, 2013, now Pat. No. 9,000,380.

(51) Int. Cl.
| | |
|---|---|
| *A61B 5/00* | (2006.01) |
| *A61B 6/10* | (2006.01) |
| *G01V 11/00* | (2006.01) |
| *G01N 22/00* | (2006.01) |
| *G01N 29/06* | (2006.01) |
| *G01V 5/00* | (2006.01) |
| *G01N 23/04* | (2006.01) |

(52) U.S. Cl.
CPC ............ *G01V 11/002* (2013.01); *G01N 22/00* (2013.01); *G01N 23/04* (2013.01); *G01N 29/0654* (2013.01); *G01V 5/0025* (2013.01)

(58) Field of Classification Search
CPC ................................. A61B 6/10; A61B 5/0034
See application file for complete search history.

(56) References Cited

U.S. PATENT DOCUMENTS

| | | | |
|---|---|---|---|
| 5,181,234 A | 1/1993 | Smith | |
| 5,600,303 A | 2/1997 | Husseiny et al. | |
| 5,692,029 A | 11/1997 | Husseiny et al. | |
| 5,842,987 A * | 12/1998 | Sahadevan | ............... A61B 6/00 378/209 |
| 6,035,227 A | 3/2000 | Shmueli | |
| 6,064,429 A | 5/2000 | Belk et al. | |
| 6,703,964 B2 | 3/2004 | McMakin et al. | |
| 6,870,791 B1 | 3/2005 | Caulfield et al. | |

(Continued)

OTHER PUBLICATIONS

Backscatter X-ray, from Wikipedia, the free encyclopedia (en.wikipedia.org/wiki/Backscatter_X-ray), retrieved on Jan. 21, 2013, 1 page.

(Continued)

*Primary Examiner* — Casey Bryant

(57) ABSTRACT

A method for scanning an individual with a security device includes providing a scanner, engaging the scanner in a first scanning mode to produce an initial scan of the individual with a controller, producing an initial representation based on the initial scan, determining a property of a second scanning mode based on information from the initial representation, and engaging the scanner in the second scanning mode to produce a second scan of the individual.

39 Claims, 10 Drawing Sheets

(56) References Cited

U.S. PATENT DOCUMENTS

| | | |
|---|---|---|
| 6,965,340 B1 | 11/2005 | Baharav et al. |
| 7,016,473 B1 | 3/2006 | Linev et al. |
| 7,119,731 B2 | 10/2006 | Fleisher |
| 7,135,980 B2 | 11/2006 | Moore et al. |
| 7,145,506 B2 | 12/2006 | Holt et al. |
| 7,253,766 B2 | 8/2007 | Foote et al. |
| 7,340,293 B2 | 3/2008 | McQuilkin |
| 7,365,672 B2 | 4/2008 | Keller et al. |
| 7,405,692 B2 | 7/2008 | McMakin et al. |
| 7,605,709 B2 | 10/2009 | Tolliver |
| 7,645,992 B2 | 1/2010 | Lyubchik et al. |
| 2002/0196141 A1 | 12/2002 | Boone et al. |
| 2004/0114130 A1 | 6/2004 | Nguyen et al. |
| 2005/0031080 A1* | 2/2005 | Klingenbeck-Regn A61B 5/1072 378/95 |
| 2005/0031082 A1 | 2/2005 | Haaga et al. |
| 2005/0052948 A1 | 3/2005 | Caulfield et al. |
| 2005/0110672 A1* | 5/2005 | Cardiasmenos ... G01N 21/3581 342/27 |
| 2006/0058645 A1 | 3/2006 | Komistek et al. |
| 2006/0087439 A1 | 4/2006 | Tolliver |
| 2006/0164285 A1 | 7/2006 | Fleisher |
| 2006/0164286 A1 | 7/2006 | Nikulin |
| 2006/0164287 A1 | 7/2006 | Holt et al. |
| 2007/0081630 A1 | 4/2007 | Evron |
| 2007/0106154 A1* | 5/2007 | Conti .................. G01T 1/1611 600/436 |
| 2007/0211192 A1 | 9/2007 | Ahn |
| 2007/0211922 A1 | 9/2007 | Crowley et al. |
| 2007/0235652 A1 | 10/2007 | Smith |
| 2008/0009731 A1 | 1/2008 | Maschke |
| 2008/0185525 A1 | 8/2008 | Lyubchik et al. |
| 2008/0253531 A1 | 10/2008 | Boyden et al. |
| 2008/0315874 A1 | 12/2008 | Crowley |
| 2009/0216117 A1* | 8/2009 | Koyama ............... A61K 49/221 600/431 |
| 2010/0034451 A1 | 2/2010 | Hughes |
| 2010/0039309 A1 | 2/2010 | Carter et al. |
| 2010/0141502 A1 | 6/2010 | Cardiasmenos et al. |

OTHER PUBLICATIONS

How Backscatter X-ray Systems Work, from internet URL: electronics.howstuffworks.com/gadgets/high-tech-gadgets/backscatter-x-ray1.htm, retrieved on Jan. 21, 2013, 3 pages.

ProVision® 2 Compact Advanced People Screening, L3 Security & Detection Systems, 2012, 3 pages.

Rez et al., "The Dose from Compton Backscatter Screening", School of Life Sciences, date unknown, 19 pages.

What is backscattering?, from arstechnica.com (arstechnica.com/science/2010/12/the-physics-and-biology-of-the-tsas-backscatter-se . . . ), retrieved on Jan. 19, 2013, 4 pages.

PCT International Search Report, International App. No. PCT/US2014/037802, dated Feb. 10, 2015, pp. 1-3.

* cited by examiner

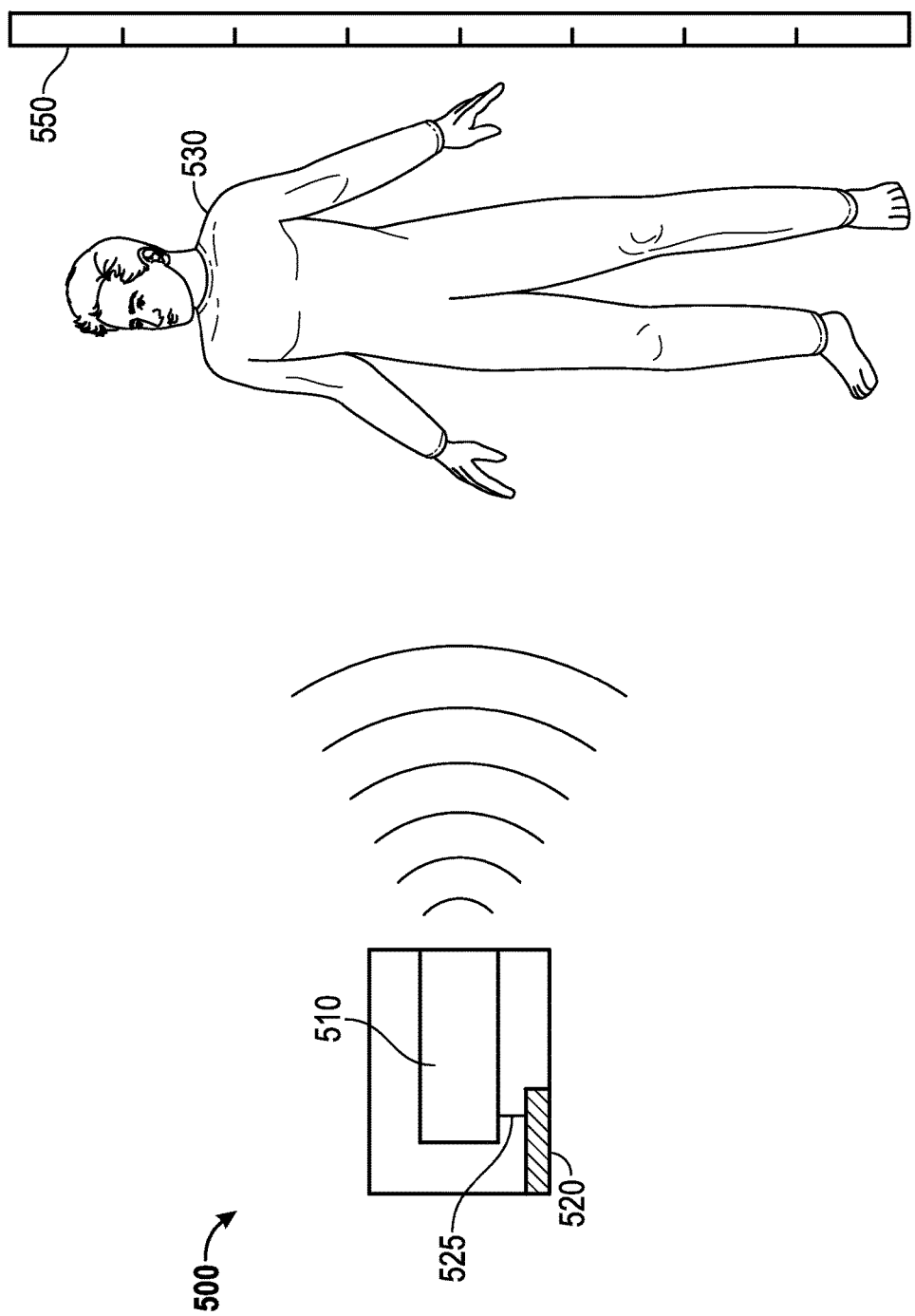

SECURITY SCANNING DEVICE

CROSS-REFERENCE TO RELATED PATENT APPLICATIONS

This application is a continuation of U.S. application Ser. No. 14/675,427, filed Mar. 31, 2015, which is a continuation of U.S. application Ser. No. 13/895,596, filed May 16, 2013, both of which are incorporated herein by reference in their entireties.

BACKGROUND

Security scanning systems (e.g., airport scanning devices, checkpoint scanning devices, and other security scanning devices) are used to determine whether a target (e.g., person, animal, etc.) possesses contraband substances. Contraband substances may include materials, weapons, currency, or other products that may be illegal or may pose a risk to other individuals. Targets may attempt to conceal contraband substances beneath a layer of clothing or internally within a body cavity or a digestive tract. Scanning systems are intended to identify those individuals who possess contraband substances before such individuals engage in air travel, pass through a checkpoint, or cause harm to others.

Traditional systems for scanning individuals include metal detectors. Metal detectors operate by generating electromagnetic fields that interact with metallic objects. Sensors within the metal detector provide feedback to an alarm that indicates the presence of a metallic object. However, these systems may not detect all types of contraband and may lack the resolution needed to effectively provide comprehensive screening.

Other systems for scanning individuals include x-ray sources or wave generators. Systems employing non-radioactive wave generators (e.g., millimeter wave scanners) may not consider specific attributes of the target when scanning. Such a lack of consideration may impact the accuracy or efficiency of the scanning device. In other systems employing an x-ray source, a dosage may be applied without considering the unique characteristics of the person. Because traditional x-ray systems do not tailor the scan to the unique attributes of the person, such systems may cause the person to receive an inappropriate dose of radiation. By way of example, the risks associated with a pregnant woman receiving a particular dose of radiation may be greater than those associated with a man receiving the same dose. Such risks may include the risk of exposing the unborn child to an elevated dosage of radiation, among others.

SUMMARY

One embodiment relates to a method for scanning an individual with a security device that includes providing a scanner, engaging the scanner in a first scanning mode to produce an initial scan of the individual with a controller, producing an initial representation based on the initial scan, determining a property of a second scanning mode based on information from the initial representation, and engaging the scanner in the second scanning mode to produce a second scan of the individual.

Another embodiment relates to a security device that includes a scanner and a controller. The controller is configured to: engage the scanner in a first scanning mode to produce an initial scan of an individual, produce an initial representation based on the initial scan, determine a property of a second scanning mode based on information from the initial representation, and engage the scanner in the second scanning mode to produce a second scan of the individual.

Still another embodiment relates to a method for detecting threats with a security device that includes providing a scanner, engaging the scanner in a first scanning mode to produce an initial scan of an individual with a controller, producing an initial representation of the individual based on the initial scan, determining a property of a second scanning mode based on information from the initial representation, and engaging the scanner in the second scanning mode to produce a second scan of the individual. The second scan is more focused than the initial scan.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The invention will become more fully understood from the following detailed description taken in conjunction with the accompanying drawings wherein like reference numerals refer to like elements, in which:

FIG. 10 is a schematic view of a detection device including a measuring device, according to another embodiment.

DETAILED DESCRIPTION

Before turning to the figures, which illustrate the embodiments in detail, it should be understood that the application is not limited to the details or methodology set forth in the description or illustrated in the figures. It should also be understood that the terminology is for the purpose of description only and should not be regarded as limiting.

Figure 1:
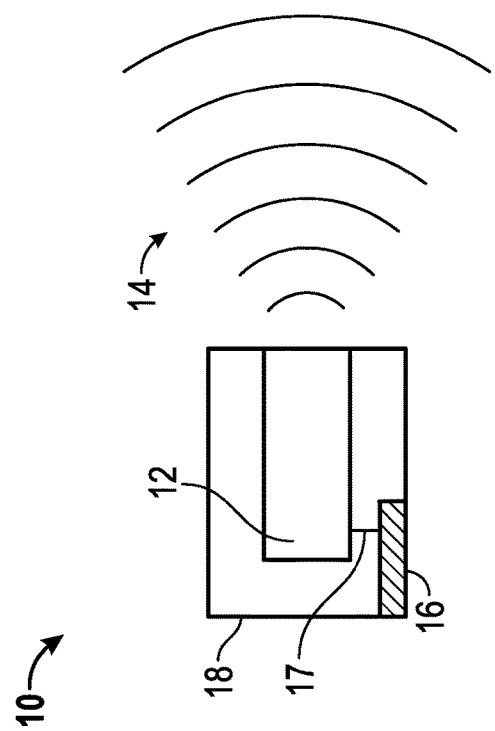
FIG. 1 is a schematic view of a detection device and a target, according to one embodiment.
Figure 1:
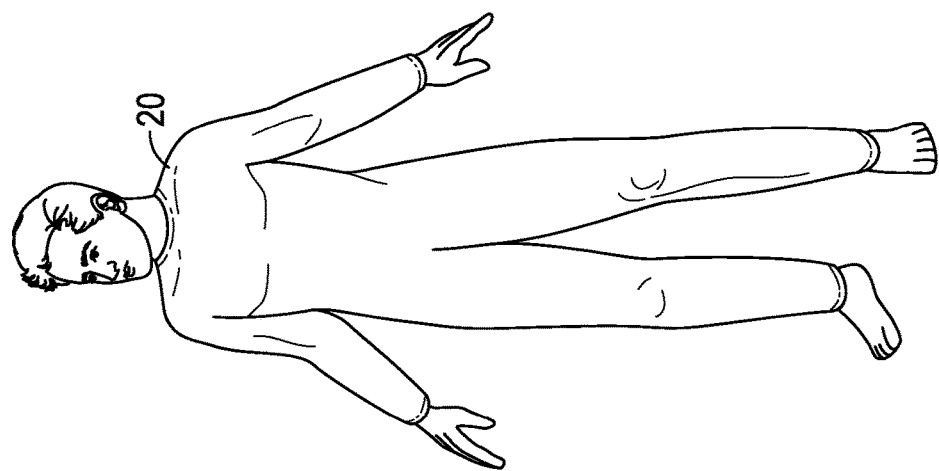

Referring to the embodiment shown in FIG. 1, a detection device, shown as detector 10 directs a scanning beam toward a target, shown as person 20. While person 20 is shown in FIG. 1, it should be understood that detector 10 may scan other living objects (e.g., animals, plants, etc.) or non-living objects (e.g., laptop computers, etc.). Detector 10 employs a scanning beam of electromagnetic waves to facilitate a determination of whether person 20 is carrying contraband material (e.g., liquids, gels, plastics, powders, metals, ceramics, weapons, explosives, drugs, currency, papers, etc.). Such a determination may be conducted by an operator utilizing detector 10 or may be conducted automatically by processing electronics within detector 10. In either embodiment, detector 10 may reduce the risk of person 20 carrying contraband material into a secured area by identifying potential threats.

According to the embodiment shown in FIG. 1, detector 10 includes a scanner, shown as scanner 12. In some embodiments, includes a generator (e.g., transducer, x-ray source, a cobalt-60 source, etc.) configured to produce a scanning beam and a sensor (e.g., detector, antenna, etc.) configured to receive and detect a returned beam that is transmitted, reflected, scattered, or otherwise deflected. The scanner also provides a signal representative of the returned beam. As shown in FIG. 1, scanner 12 directs a scanning beam of incident waves, shown as incident waves 14, toward person 20. Scanner 12 may deliver a beam that is static (e.g., having a fixed, non-moving spatial pattern, etc.) or may deliver a beam that is dynamic (e.g., having a spatial pattern that varies or moves) during the examination. It should be understood that such incident waves 14 may facilitate the imaging of person 20 and the detection of contraband material.

According to one embodiment, scanner 12 directs incident waves 14 having parameters (e.g., whether the waves are ionizing radiation, intensity, flux, power level, frequency, image resolution, etc.). In some embodiments, the parameters of incident waves 14 cause a person to receive a radiation dose (e.g., as measured in millirems, milliseverts, etc.). In other embodiments, the incident waves 14 expose the person to non-ionizing radiation and the parameters include intensity, frequency, image resolution, or other features of non-ionizing electromagnetic waves.

As shown in FIG. 1, detector 10 includes a controller (e.g., module, command device, processing electronics, processing circuit, etc.), shown as controller 16. According to one embodiment, controller 16 is coupled to scanner 12 with a communication link, shown as data link 17. Controller 16 may communicate with scanner 12 through data link 17. By way of example, controller 16 may send a signal to engage scanner 12 thereby producing a scanning beam. Controller 16 may also receive a signal from scanner 12 relating to a returned beam. According to one embodiment, controller 16 receives and analyzes the received signal as part of a contraband detection scheme.

Referring still to the embodiment shown in FIG. 1, detector 10 includes a housing 18. Housing 18 provides structural support for various components of detector 10. By way of example, housing 18 may include sidewalls (e.g., to prevent person 20 from approaching scanner 12, to otherwise position person 20 relative to scanner 12, etc.) or may include a floor portion (e.g., to provide a platform for person 20 to stand upon, etc.). While shown in FIG. 1 as having a rectangular cross section and defining a hollow interior, it should be understood that housing 18 may have various shapes and may include still other portions. As shown in FIG. 1, controller 16 and scanner 12 are coupled to housing 18. In some embodiments, housing 18 partially surrounds scanner 12. According to one embodiment, housing 18 includes a shield configured to absorb ancillary electromagnetic radiation produced by scanner 12.

According to one embodiment, scanner 12 produces x-rays (e.g., an x-ray tube, an x-ray source, etc.). In some embodiments, the scanner is a low-power x-ray source (e.g., 50 kV, 100 kV, 120 kV, 200 kV, etc.) configured to produce a low energy x-ray beam. The x-ray beam may be directed toward person 20, where incident x-rays or photons interact with tissue of person 20. In some embodiments, the incident x-rays or photons ionize atoms of person 20 and produce lower-energy fluorescence photons. It should be understood that reflected waves and scattered photons (i.e. a reflected beam) may be detected by scanner 12 to facilitate detecting contraband (i.e. backscatter x-ray imaging). In other embodiments, the scanner includes a higher energy source to facilitate transmissive x-ray imaging. According to still other embodiments, scanner 12 may include another type of ionizing source (e.g., ultraviolet, gamma, etc.) or may include a non-ionizing source (e.g., a laser transmitter, an ultrasonic wave transmitter, a terahertz wave transmitter, a microwave scanner, a radio wave transmitter, an infrared wave transmitter, etc.).

It should be understood that person 20 may receive a dose of radiation (i.e. deposited energy) during operation of detector 10. Various recommendations have been made regarding a person's preferred maximum exposure to radiation. By way of example, the United States federal occupational limit of total effective dose equivalent per year (i.e. the total allowable dose) may be 5,000 millirems for an adult, 500 millirems for a minor working with radiation, and 50 millirems per month of gestation for an unborn child with a maximum of 500 millirems during the entire gestation. While provided in millirems, doses of radiation may be measured in milliseverts or in still another unit. Doses of radiation may be denoted in units of deposited energy per mass, energy per volume, or in still other units. Individual portions of the body may also have dose limitations. By way of example, a deep-dose equivalent, eye dose equivalent, shallow-dose equivalent to the skin, a shallow-dose equivalent to an extremity, or a dose equivalent for a particular organ may be computed and regulated. Similar to the total effective dose equivalent, these area specific dose limitations may vary for adults, children, pregnant women, or still other categories of individuals.

As shown in FIG. 1, person 20 includes various characteristics. By way of example, such characteristics include the age, weight, gender, ID, and body structure, among other features. According to one embodiment, such characteristics also include whether person 20 is pregnant, and whether person 20 has health conditions. These and other characteristics may impact whether a scanning beam applied by detector 10 may cause person 20 to receive a total effective dose equivalent or area-specific dose equivalent in excess of a recommended annual maximum (i.e. the allowable dosage may be measured on an annual basis) or another preferred limit for person 20. By way of example, an elderly person may have skin that is thinner than a younger person, and x-rays may achieve a reduced penetration depth for a person having an increased body mass index (i.e. a heavier person) than for a slender person. By way of example, the allowable dosage may be less for a child or for a pregnant woman, than for an adult male.

According to one embodiment, the scanning beam applied by scanner 12 of detector 10 may vary based on the allowable dosage and/or at least one characteristic of person 20. In some embodiments, the scanning beam applied by scanner 12 may vary based on a physical characteristic of person 20 (e.g., height, weight, body mass index, a pregnancy status, etc.). The relation between allowable dose and the characteristic of the person can be determined from a database, a lookup table, an algorithm, or similar relationships. In other embodiments, the scanning beam applied by scanner 12 may vary based on a total effective dose equivalent limit for person 20. According to one embodiment, the scanning beam may also be varied based on at least one of a previous dose (e.g., a dose received during a current travel itinerary, a dose received during recent travels, a dose received during medical or other non-travel related scanning, etc.), an anticipated future dose (e.g., a dose to be received during a current travel itinerary, a dose to be received during future travels, a dose to be received during medical or other non-travel related scanning, etc.), and based on the likelihood that person 20 may be exposed to the total allowable dose (e.g., based on lifestyle, occupation, residence, other features of the individual's lifestyle, etc.). In some embodiments, controller 16 utilizes at least one of the total allowable dose, a previous dose, an anticipated future dose, a cumulative dosage over a time period, a cumulative dosage over a number of scanning sessions, and the likelihood that person 20 may be exposed to the total allowable dose to determine the output of scanner 12.

Figure 2B:
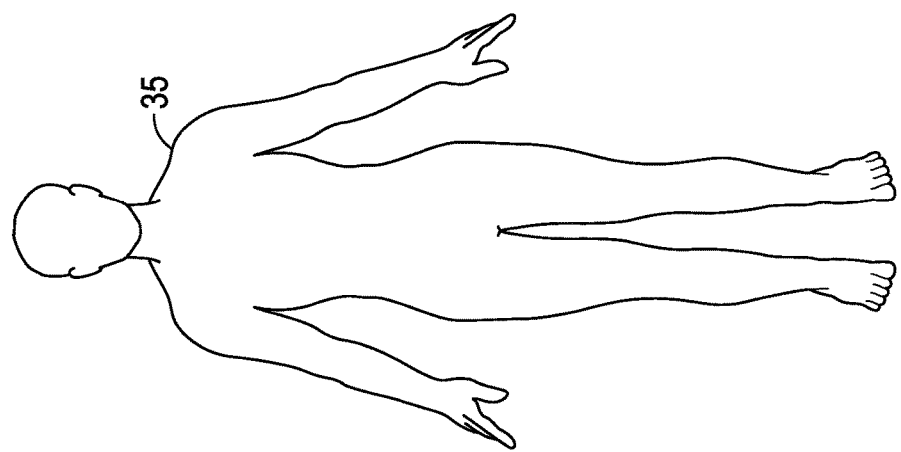
FIGS. 2a-2b are elevation views of a target and a corresponding schematic, according to one embodiment.
Figure 2A:
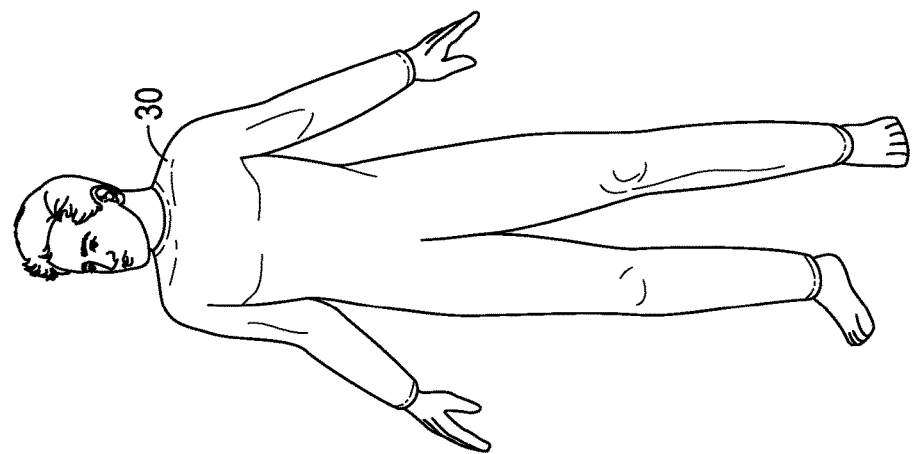

Referring next to the embodiment shown in FIGS. 2a-2b, a controller of a detection device provides a command signal to a scanner. The command signal includes specified information relating to the operation of the scanner. By way of example, the command signal may include information regarding the desired resolution and a signal to noise ratio of the scanner. It should be understood that the desired resolution, signal to noise ratio, or other feature of the command signal may impact the dose received by the target. According to one embodiment, an increased desired resolution similarly increases the dose received by the target. In some embodiments, the controller may tailor the command signal based on a characteristic of the individual.

According to one embodiment, the desired resolution may be reduced to reduce the dose received by an elderly person or by a child. According to another embodiment, the desired resolution may be reduced to reduce the dose received by a pregnant woman due to the risk of radiation exposure to the unborn child. According to still another embodiment, various other features of the command signal may be varied based on characteristics of the target. It should be understood that the controller may alternatively transmit the command signal to an additional device (e.g., processor, compiler, modulator, transceiver, control device, etc.) in communication with the scanner. Such an additional device may be coupled to or integrated with the scanner and may decode or otherwise interpret the command signal.

Referring to FIG. 2a, the detector may direct the scanning beam toward the target, shown as person 30. As discussed above, the detector may include a sensor (e.g., detector, antenna, etc.) configured to receive waves. According to one embodiment, the detector includes processing electronics, and the sensor provides a signal indicative of the received waves to the processing electronics. In some embodiments, the processing electronics may receive the signal and produce a schematic (i.e. mannequin, dummy, outline, figure, etc.) of person 30. Such a schematic, shown in FIG. 2b as schematic 35, may include only a two-dimensional outline of person 30. In other embodiments, schematic 35 comprises a three-dimensional model of person 30. According to one embodiment, the detector displays schematic 35 to an operator (e.g., for review). According to another embodiment, the detector displays a more detailed representation of person 20 to an operator (e.g., an image as compiled by the processing electronics and showing the outline or other features of person 30).

Figure 3A:
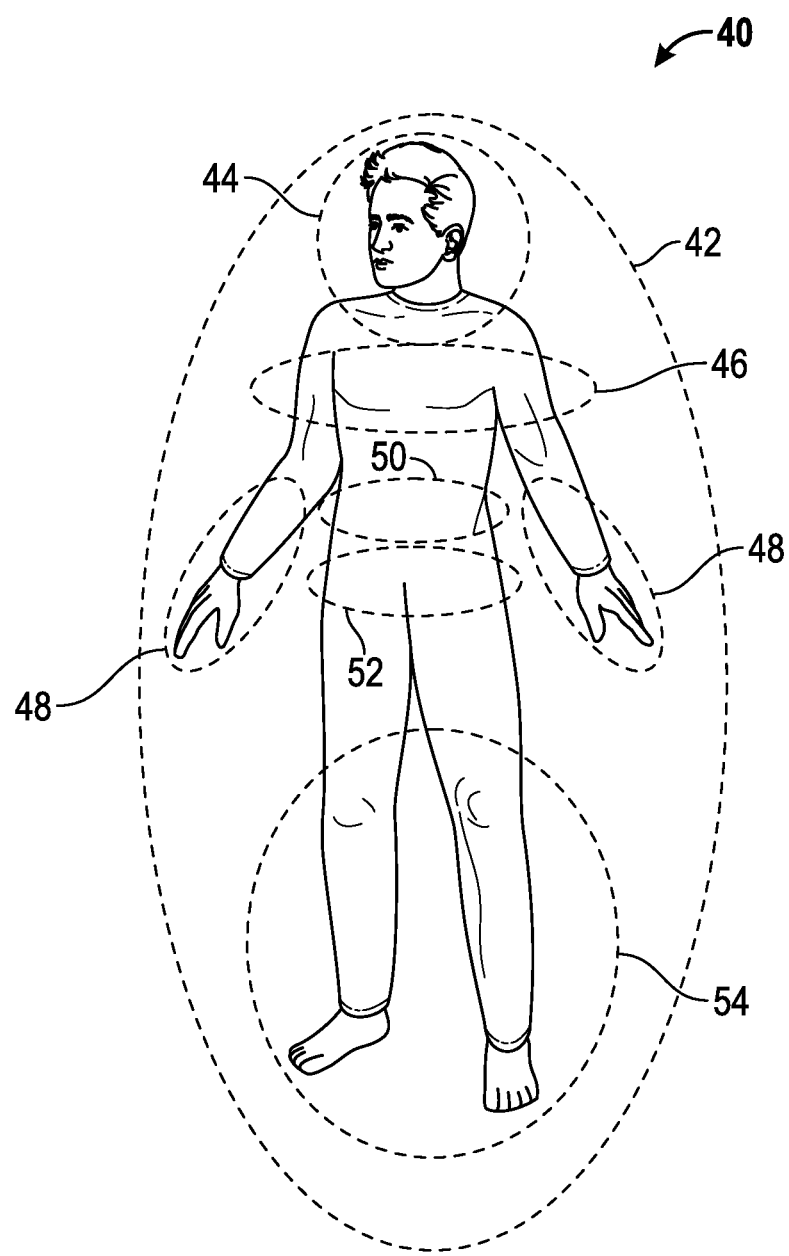
FIG. 3a is a schematic view of a target having a plurality of scanning regions, according to one embodiment.

Referring next to FIG. 3a, a target, shown as person 40, may include a plurality of scanning regions. As discussed above, different portions of person 40 may have different maximum effective dose limits. According to one embodiment, person 40 includes an entire body region, shown as total body area 42, an upper region, shown as head area 44, and a chest region, shown as chest area 46. As shown in FIG. 3, person 40 also includes an upper extremity region, shown as upper extremity area 48, an abdominal region, shown as abdominal area 50, a pelvic region, shown as pelvic area 52, and a lower extremity region, shown as lower extremity area 54. Various factors may impact a previous or anticipated future exposure for at least a portion of person 40. For example, person 40 may have recently had a mammogram or chest x-ray thereby causing chest area 46 to receive an effective dose of radiation. In another example, person 40 may have underwent a computed tomography head scan thereby causing head area 44 to receive an effective dose of radiation. In another example, anticipated future surgeries, travels, or other activities may impact an anticipated future exposure of at least a portion of person 40.

Figure 3B:
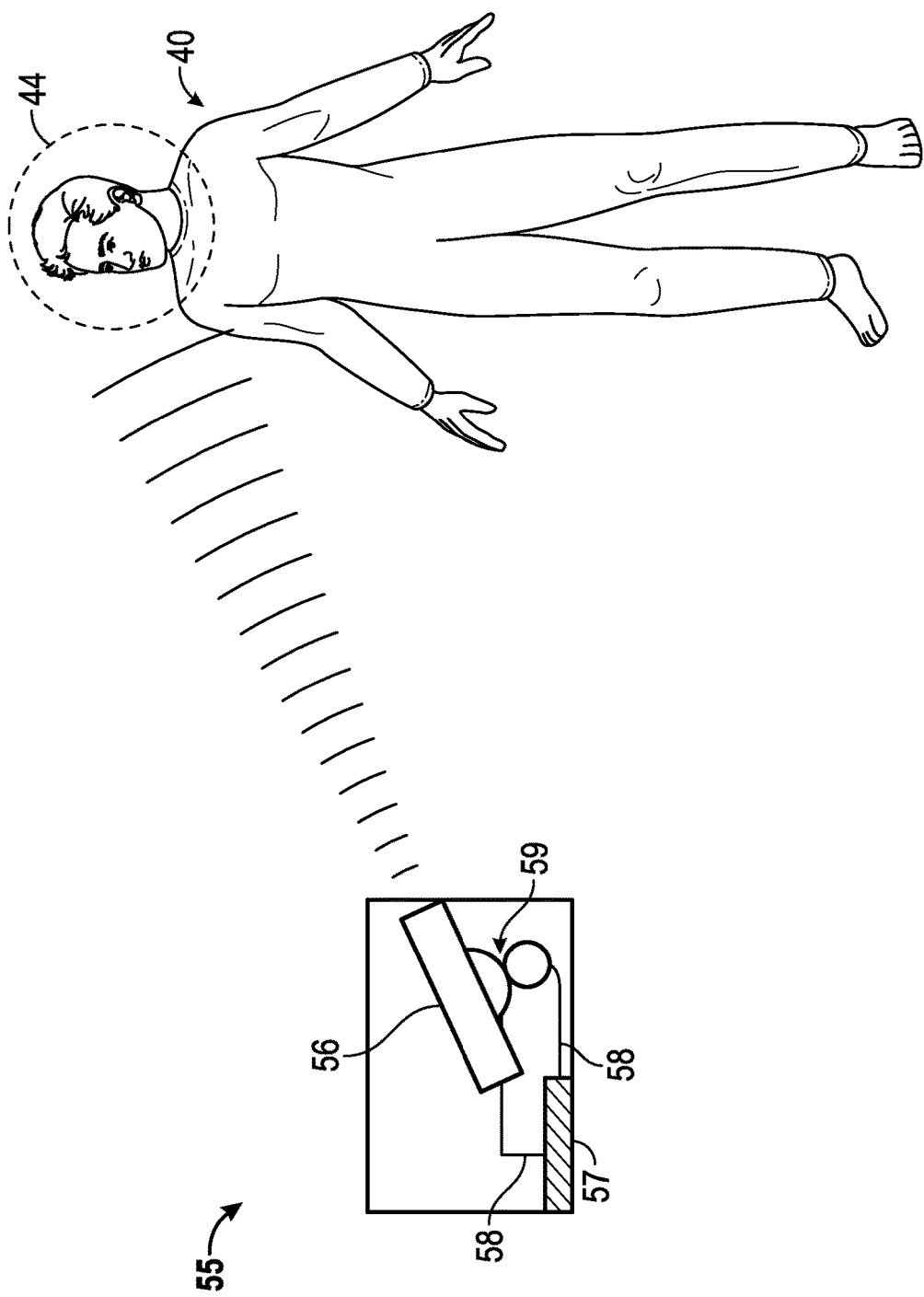
FIG. 3b is a schematic view of a detection device including a driver, according to one embodiment.

According to the embodiment shown in FIG. 3b, a detector, shown as detector 55 includes a scanner, shown as scanner 56 coupled to a controller 57 with a data link, shown as cable 58. As shown in FIG. 3b, detector 55 includes a driver, shown as actuator 59. According to one embodiment, actuator 59 is a stepper motor. According to another embodiment, actuator 59 is another device configured to facilitate relative movement between scanner 56 and person 40. In some embodiments, actuator 59 is also coupled to controller 57 with cable 58. Such coupling may allow controller 57 to simultaneously control both scanner 56 and actuator 59 to, by way of example, facilitate associating a particular orientation of scanner 56 with particular waves. According to one embodiment, actuator 59 is configured to direct scanner 56 toward a portion of person 40. As shown in FIG. 3b, actuator 59 directs scanner 56 toward head area 44 of person 40. Such direction may occur as part of a total body scan of person 40 (e.g., an initial scan, an entire body rescan, etc.) or may facilitate detector 55 scanning of only a portion of person 40 (e.g., due to poor image quality of an initial scan, where a detector identifies potential contraband, etc.).

According to one embodiment, a historical or anticipated future exposure for at least one portion of person 40 may be considered as part of a contraband detections scheme. Such consideration may result in reducing the intensity, signal to nose ratio, resolution, or other feature with a command signal based on the historical or anticipated future exposure. According to one embodiment, the detector initially scans only a portion of person 40 (e.g., may not scan abdominal area 50 where person 40 is pregnant, etc.). According to another embodiment, the detector initially scans total body area 42 (e.g., to produce an initial schematic of person 40). In some embodiments, the detector may thereafter scan total body area 42 to, by way of example, improve the quality of the schematic of person 40 (i.e. apply a uniform scanning beam to person 40). In other embodiments, the detector may thereafter scan only a portion (e.g., abdominal area 50, pelvic area 52, etc.) of total body area 42 or may thereafter scan different portions of total body area 42 with different scanning beams (i.e. apply a non-uniform scanning beam). Such additional partial scanning may correspond to areas of person 40 where, by way of example, the image quality of the initial scan is below a threshold level or where the detector finds an indication of contraband, among other reasons warranting additional scanning.

In some embodiments, the detector includes processing circuits having logic configured to employ a contraband detection scheme that considers the costs of scanning person 40. According to one embodiment, the contraband detection scheme also considers the benefits of scanning person 40. As discussed above, the costs of scanning a person may include previous or future doses, whether the person is pregnant, medical conditions, or still other factors. Such costs may be impacted by a characteristic or physical condition of person 40.

According to one embodiment, the detector associates reduced risks with scanning an organ of a person 40 having an increased body mass index (i.e. waves may be absorbed by outer layers of fatty tissue thereby insulating internal organs), whereas a detector may associate increased risks with scanning an organ of a thin elderly person 40 (i.e. the thin skin of an elderly person may allow more waves to pass through and interact with internal organs). Such reduced risks may reduce the cost of scanning person 40 having a larger body mass index relative to the cost of scanning a thin elderly person 40. By way of an additional example, a detector may associate a higher cost to scanning chest area 46 for a woman who recently had a mammogram than for a woman who did not recently have a mammogram. As still another example, a detector may associate a higher cost to scanning abdominal area 50 of a pregnant woman. Various benefits of scanning or rescanning person 40 include detection of contraband, improving the quality of the initial scan, improving a confidence in whether person 40 is carrying contraband, and improving a confidence in the identity of the contraband, and among other potential benefits.

It should be understood that the contraband detection scheme may associate various numerical values to potential characteristics of person 40 and compare a cost total with a benefit total associated with the reason for scanning or rescanning a portion of person 40 (e.g., a value associated with a certainty of contraband located within the area, a value associated with the danger of such contraband, etc.). In some embodiments, the contraband detection scheme may scan or rescan a portion of person 40 (e.g., chest area 46) after weighing the costs and benefits of scanning that portion of person 40. According to one embodiment, such scanning or rescanning may occur automatically. According to another embodiment, the detector may wait for operator input before performing an initial scan. According to still another embodiment, the detector may rescan person 40 only after receiving an operator input (e.g., an approval of the cost versus benefit analysis).

Figure 4:
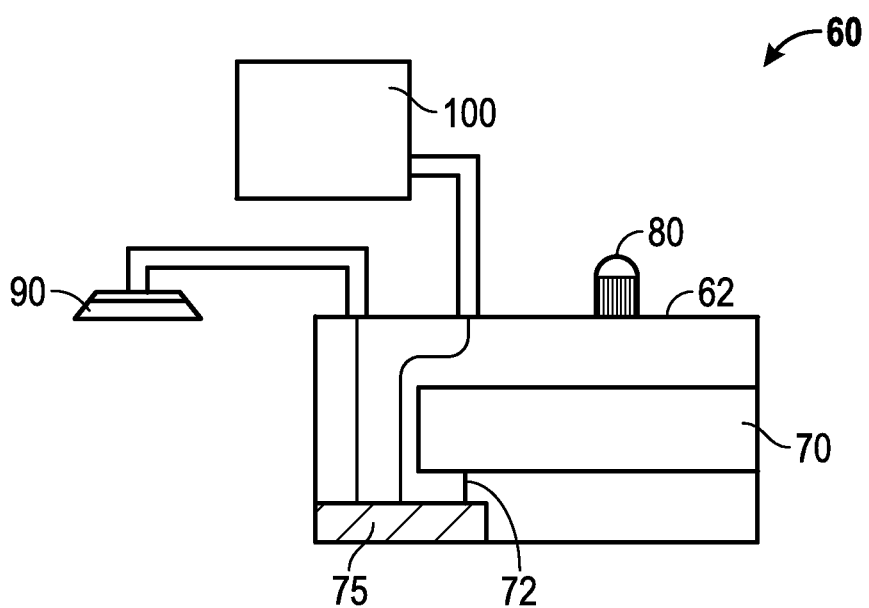
FIG. 4 is a schematic view of a detection device including an indicator, an identifier, and an input device, according to one embodiment.

Referring next to the embodiment shown in FIG. 4, a detection device, shown as detector 60, includes a plurality of components configured to facilitate targets (e.g., persons, individuals, etc.) for contraband. As shown in FIG. 4, detector 60 includes a scanner, shown as scanner 70 positioned within a housing, shown as housing 62. In some embodiments, scanner 70 emits and receives waves that interact with the target. According to the embodiment shown in FIG. 4, detector 60 includes a controller (i.e. module, command device, processing electronics, etc.), shown as controller 75. Controller 75 may be coupled to scanner 70 with a data link, shown as data cable 72. In some embodiments, controller 75 may be configured to send command signals to, by way of example, a generator within scanner 70 and receive data signals from, by way of example, a sensor within scanner 70.

According to the embodiment shown in FIG. 4, detector 60 includes an indicator, shown as contraband notification device 80, configured to alert an operator (e.g., a person operating detector 60, a remote person monitoring detector 60, etc.) of the potential that the person being scanned possesses contraband. In one embodiment, contraband notification device 80 includes a signal light coupled to an outer surface of housing 62. According to another embodiment, contraband notification device 80 may include another visual indicator. According to still another embodiment, contraband notification device 80 includes an audible alarm (e.g., a speaker configured to emit a sound as detector 60 determines that the person may possess contraband).

According to yet another embodiment, contraband notification device 80 includes a display screen (e.g., a liquid crystal display, a light emitting diode display, etc.) configured to indicate to the operator that the person may possess contraband. By way of example, such a display may show a schematic of the person and indicate the presence (and location) of contraband. According to one embodiment, the display uses an icon in the shape of the potentially detected contraband on a schematic of the person to show the operator the nature and location of the potential contraband. In some embodiments, the display is configured to show several types of contraband (e.g., a knife shape to indicate a potential knife, a drop to indicate a potential liquid, etc.). Contraband notification device 80 may operate at a first level (e.g., a first pitch, a first volume, a first color, indicate an first alarm on the display, etc.) to indicate the presence of a first class of contraband (e.g., drugs, currency, etc.) and may operate at a second level (e.g., a second pitch, a second volume, a second color, indicate a second alarm on the display, etc.) to indicate the potential presence of a second class of contraband (e.g., explosives, liquids, weapons, etc.). It should be understood that contraband notification device 80 may include still other components to indicate the potential presence of contraband.

Referring still to the embodiment shown in FIG. 4, detector 60 includes an identifier, shown as information acquisition device 90. According to one embodiment, information acquisition device 90 is configured to acquire information about the target. Such information may include, by way of example, age, gender, a pregnancy status, a medical condition (e.g. the presence of a hip implant, a pacemaker, or another medical condition, etc.), past travel activity, future travel activity, or still other information that may be used as part of a contraband detection scheme. Such information may include identification information about the target (e.g., name, social security number, ticket number, etc.) that facilitates retrieval of other information (e.g., the information discussed above, other information, etc.) from a database or other record.

According to one embodiment, the information includes historical data relating to the number of times a scanner has detected potential contraband on the target. The information may also include historical data relating to the location and identity of contraband detected by a scanner. Such historical data may allow detector 60 to more effectively determine whether the target possesses contraband (e.g., detector 60 may scan a portion of the target where a previous scanner identified potential contraband with a greater dosage, rescan the area, etc.). According to another embodiment, the information may be used to create a summary (e.g., a numerical "threat value," an overview of previously detected contraband, the locations of previously detected contraband, etc.) of the target for use as part of a contraband detection scheme. By way of example, detector 60 may initially scan or rescan a target having a more concerning summary with a scanning beam having intensified parameters (e.g., intensity, etc.).

In some embodiments, information acquisition device 90 includes a data entry device, the data entry device configured to allow an operator (e.g., an attendant, etc.) to enter the name or other identifying information of the target. A database of information may store historical data associated with the target, which may be provided to detector 60 for use as part of a contraband detection scheme. It should be understood that the name or other identifying information of the target may be provided using another device (e.g., a keyboard, retrieved from a database along with current travel itineraries, etc.).

Information acquisition device 90 may include a barcode scanner configured to interface with a barcode associated with the target. By way of example, the barcode may be printed on the boarding pass of an airline passenger. According to another embodiment, information acquisition device 90 includes a radiofrequency antenna configured to interface with a radiofrequency tag associated with the target. Such a radiofrequency tag may be located in the identification (e.g., a driver's license, passport, etc.) of the target, among other potential locations. According to still another embodiment, information acquisition device 90 includes a quick response scanner configured to interface with a quick response code associated with the target (e.g., printed on the passenger's boarding pass, printed on an article of clothing, etc.).

In some embodiments, information acquisition device 90 facilitates the timely processing of targets through detector 60. While retrieving information from a database by inputting the target's name at detector 60 may reduce the need for barcodes, quick reference codes, or radiofrequency tags, such retrieval may take time to conduct thereby increasing processing time. Including barcode, quick reference codes, or radiofrequency tags containing a summary of the target on boarding passes or other associated materials may reduce processing time. It should be understood that the barcode, quick reference code, radiofrequency tag, or other system configured to interface with information acquisition device 90 may include an encryption technique or other system to prevent targets from altering their corresponding summary.

As shown in FIG. 4, detector 60 includes an input device (e.g., operator interface, etc.), shown as user interface 100. According to one embodiment, an operator may provide characteristics or other information about a target with user interface 100. In another embodiment, the characteristics or information may be acquired from a network or information acquisition device 90, as discussed above. According to still another embodiment, both user interface 100 and information acquisition device 90 may be utilized to determine characteristics or other information about the target.

Figure 5:
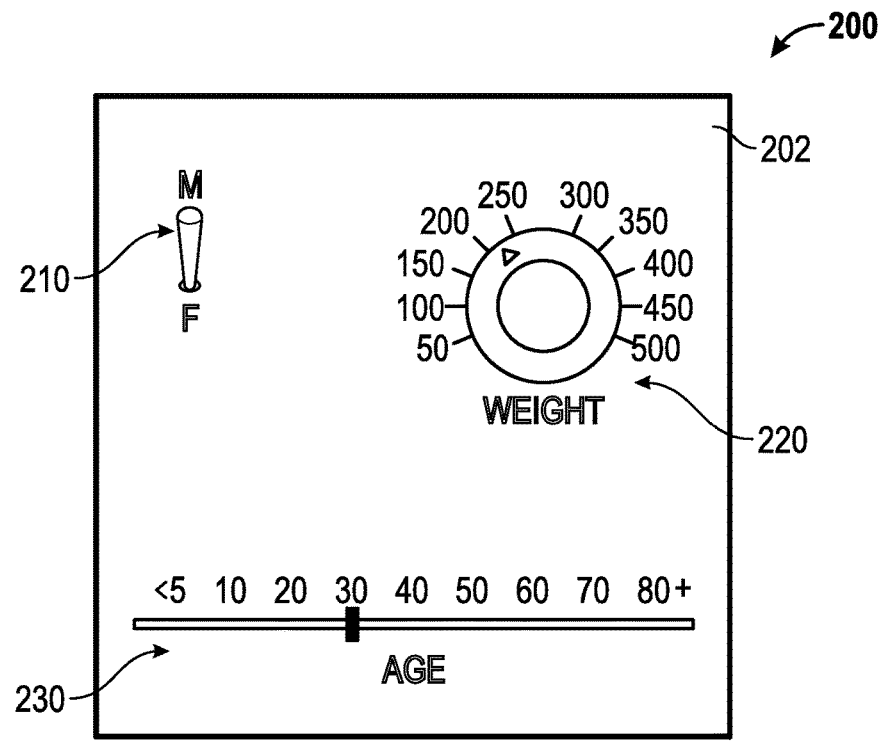
FIG. 5 is a schematic view of an input device, according to one embodiment.
Figure 6:
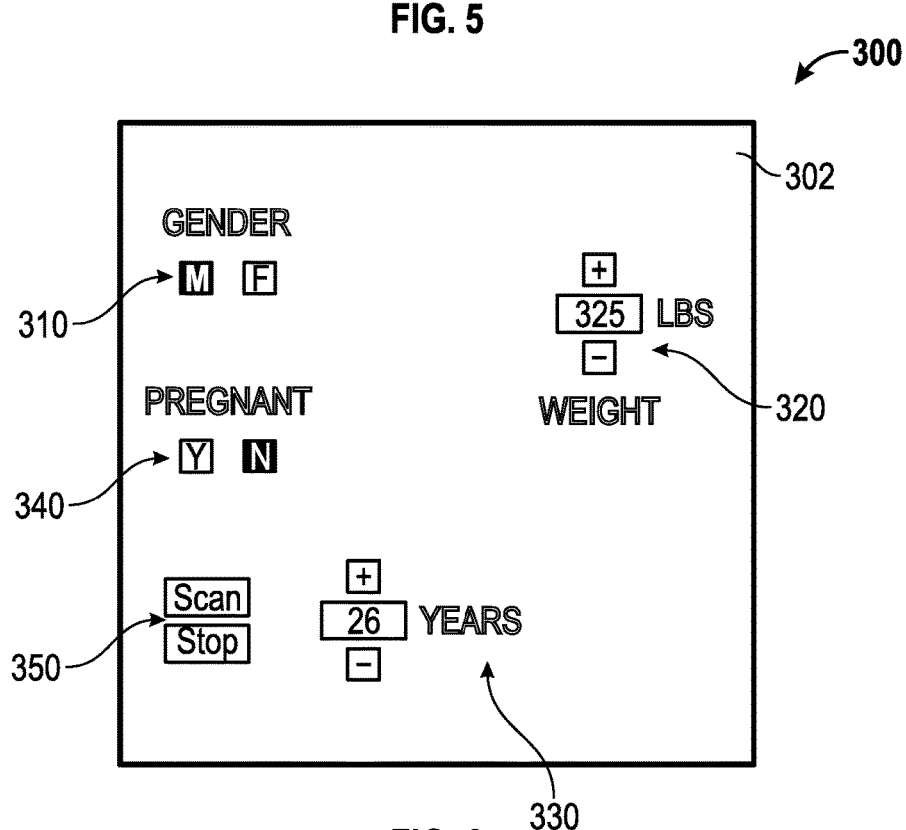
FIG. 6 is a schematic view of an input device, according to another embodiment.

Referring next to the embodiments shown in FIGS. 5-6, a detector may allow an operator to provide characteristics of the target using various types of user interfaces. Allowing the operator to provide characteristics may simplify the operation of a detector, may improve the likelihood that the characteristics apply to the target, may keep the operator engaged in the scanning activity, or may provide still other benefits. As shown in FIG. 5, an input device, shown as user interface 200, allows an operator to provide various characteristics of the target. According to one embodiment, user interface 200 displays various potential characteristics of the target (e.g., male, female, age, weight, etc.).

As shown in FIG. 5, user interface 200 includes a switch, shown as switch 210, that allows an operator to toggle between male (indicated as "M") and female (indicated as "F") to select the appropriate category for the target. According to one embodiment, user interface 200 further includes a dial, shown as dial 220, configured to allow an operator to selectively indicate a weight of the target (e.g., by turning a point on the dial toward a corresponding marking on a face of user interface 200). In other embodiments, a scale may be used to allow an operator to obtain the weight of the target. As shown in FIG. 5, user interface 200 includes a slide 230, configured to allow an operator to actuate a handle to a corresponding age of the target. According to one embodiment, switch 210, dial 220, and slide 230 are coupled to a housing, shown as housing 202 of user interface 200.

In various embodiments, at least one characteristic of the target is automatically determined by the detector (e.g., weight, etc.) and at least one characteristic of the target may be provided by the operator (e.g., gender, etc.). According to one embodiment, user interface 200 provides a characteristic signal to another component of a detector (e.g., a controller, a processing circuit, etc.) that corresponds to the operator's selection. Other components of the detector may utilize the characteristic signal as part of a contraband detection scheme (e.g., to determine the parameters of the scanning beam, etc.).

As shown in FIG. 6, an input device, shown as user interface 300, allows an operator to input various characteristics of the target. According to one embodiment, user interface 300 includes a touch screen (i.e. graphical user interface), shown as display 302. It should be understood that an operator may interact with (e.g., touch, look at, etc.) various portions of display 302 to make or confirm a selection. As shown in FIG. 6, user interface 300 includes a plurality of indicators (i.e. icons, text, etc.) corresponding to various potential characteristics of the target.

According to one embodiment, user interface 300 includes a first portion, shown as gender selection 310, defining buttons relating to the gender of the target. As shown in FIG. 6, user interface 300 also includes a portion, shown as weight portion 320, configured to show a weight of the target and operator buttons (e.g., a plus symbol to allow an operator to increase the displayed weight and a minus symbol to allow an operator to decrease the displayed weight). According to one embodiment, a portion, shown as age portion 330, displays the age of the target and operator buttons. As shown in FIG. 6, user interface includes a portion, shown as pregnancy indication 340, having buttons to allow an operator to select whether the target is pregnant (i.e. whether the person indicates that they are pregnant, whether the person appears pregnant, etc.).

According to one embodiment, user interface 300 may propagate various default selections (e.g., the shaded buttons shown in FIG. 6) for approval by the operator. In some embodiments, the default selections may be generated using information (e.g., information gathered through an information acquisition device or other identifier) for approval by the operator. In either embodiment, an operator may also initiate or cease operation of a detector using buttons positioned with a command portion, shown as command portion 350. According to one embodiment, user interface 300 provides a characteristic signal to another component of a detector (e.g., a controller, a processing circuit, etc.) that corresponds to the operator's selection. Other components of the detector may utilize the characteristic signal as part of a contraband detection scheme (e.g., to determine the parameters of the scanning beam, etc.).

As discussed above with regard to information acquisition device 90, information about the target may be acquired from a database (e.g., a database positioned on detector 60 or coupled to detector 60 with a network). In some embodiments, information about the target may be employed as part of a contraband detection scheme without revealing the information to an operator. By way of example, information obtained over a network (e.g., upon entry of the target's name) or otherwise obtained by information acquisition device 90 may be provided to a processing circuit of detector 60.

Such a technique of direct usage may provide the benefit of maintaining as confidential the information of the target (i.e. a target may have a privacy interest, such as a protected privacy interest in personal medical information, in at least a portion of the information, etc.). However, automatic use of the information may present the risk that a target will receive an inappropriate dose where the summary includes incorrect or outdated information. A scanning beam may cause the target to receive an inappropriate dose where, by way of example, the target has recently lost weight. Detector 60 may utilize the previous weight of the target and determine that a scanning beam that will cause the target to receive a larger dose may be appropriate (e.g., fatty tissue absorbs waves and photons more than skin alone) where such a scanning beam may not be appropriate given the current body mass of the target.

According to another embodiment, all of the information from the summary is presented on a user interface for review by the operator. After the operator verifies the information, a detector may utilize the information as part of a contraband detection scheme. According to another embodiment, a portion of the information may be presented on a user interface for review by the operator and a portion of the information may be directly incorporated into the contraband detection scheme. Such information provided to the operator for verification may include data not protected by health privacy laws (e.g., weight, height, age, gender, etc.) or may include other information (e.g., whether the person is pregnant, etc.).

Figure 7:
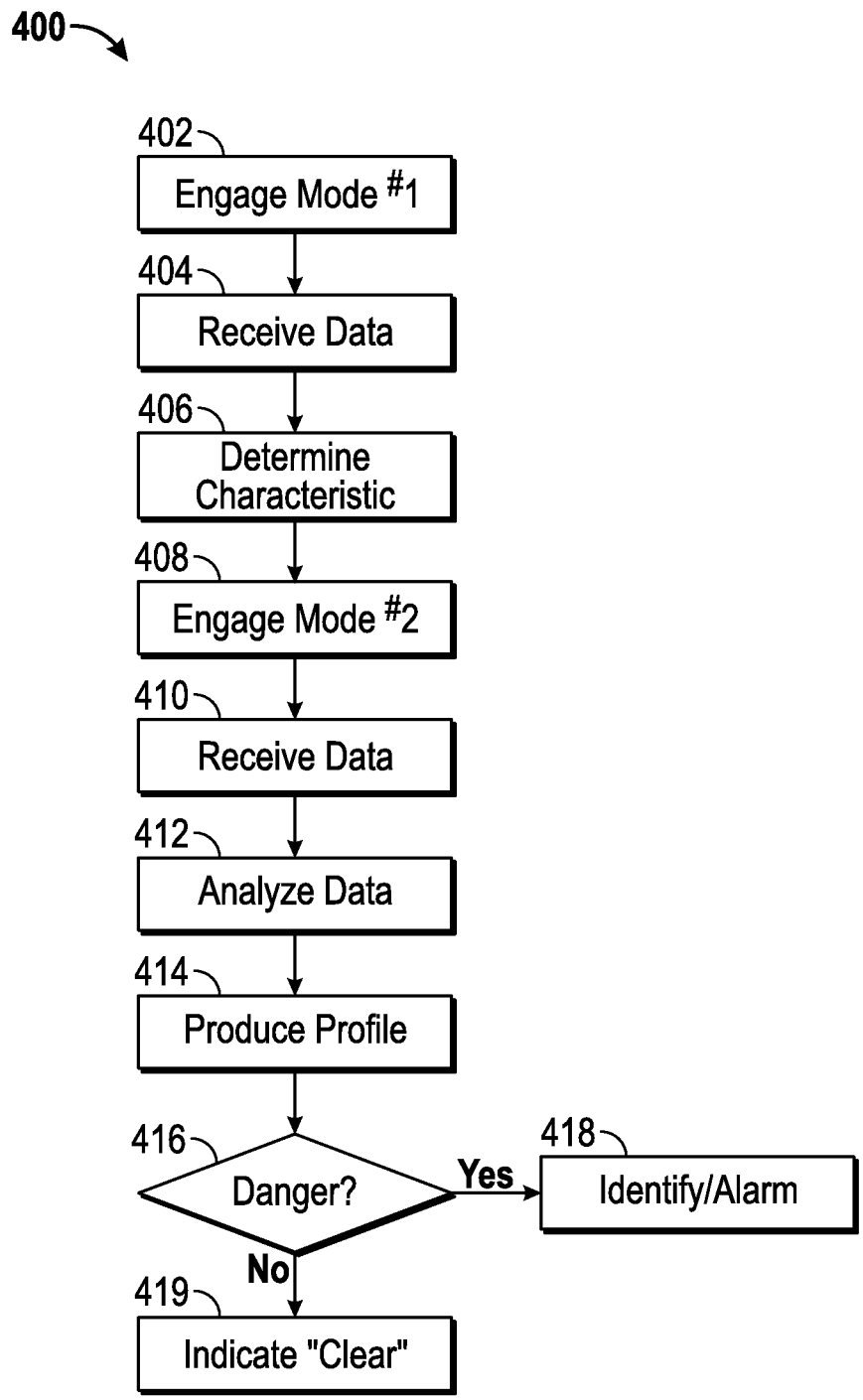
FIG. 7 is a flow diagram illustrating a contraband detection scheme, according to one embodiment.
Figure 8:
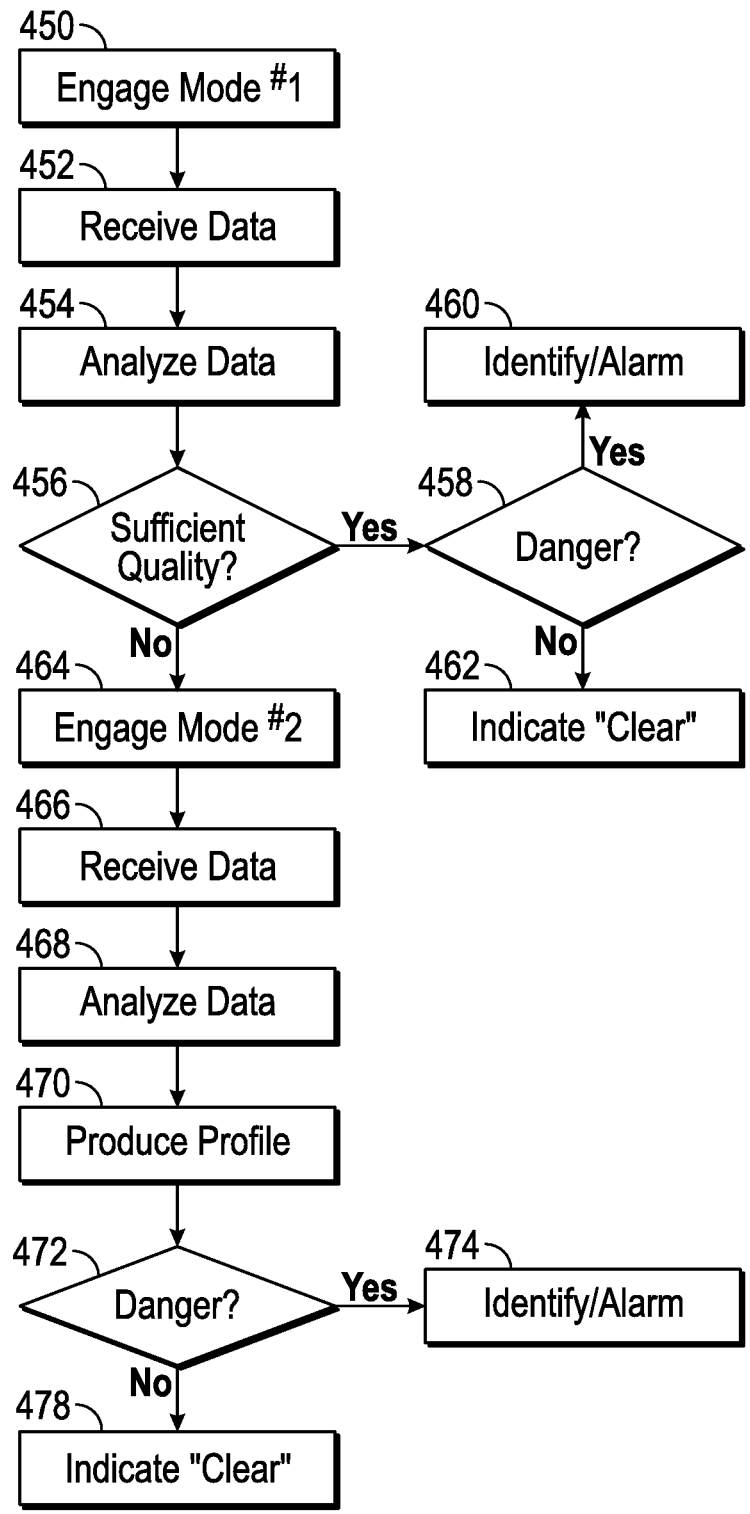
FIG. 8 is a flow diagram illustrating a contraband detection scheme, according to another embodiment.

Referring next to the embodiment shown in FIGS. 7-8, a detector is configured to perform a first scan (i.e. an initial scan) and thereafter perform a second scan (i.e. a secondary scan). As shown in FIG. 7, the detector operates in a first scanning mode to produce the initial scan and operates in a second scanning mode to produce the second scan. According to one embodiment, the detector includes a photon generator. In some embodiments, the photon generator comprises an x-ray device (e.g., a backscatter x-ray source). In other embodiments, the photon generator includes a non-radioactive device (e.g., an optical scanner, a millimeter wave scanner, etc.). A photon generator may operate at a first level (e.g., frequency, intensity, amount of radiation, etc.) in the first scanning mode and operate at a second level in a second scanning mode.

According to another embodiment, the detector includes a first wave or photon generator and a second wave or photon generator. In some embodiments, at least one of the first wave or photon generator and the second wave or photon generator includes an x-ray device. According to one embodiment, the detector operates a non-ionizing wave or photon generator during the first scanning mode and operates an x-ray device in the second scanning mode. Such operation may allow the detector to conduct an initial scan without causing the target to receive a dose. Thereafter, the target may receive a dose during the second scanning mode (e.g., where the detector identifies potential contraband, where the quality of the initial scan is below a threshold value, etc.). In other embodiments, neither of the first wave or photon generator and a second wave or photon generator includes an x-ray source. According to one embodiment, the detector operates the first wave or photon generator (e.g., a radio wave optical scan, a biometric identification scanner) during the first scanning mode and operates the second wave or photon generator (e.g., a millimeter scanner, etc.) during the second scanning mode.

Referring to FIG. 7, a controller is configured to operate a detector according to a method, shown as contraband detection scheme 400. Controller engages the first scanning mode (step 402), and waves are emitted (e.g., from a generator) toward a target. The detector receives waves (e.g., with a sensor, etc.), and the controller receives data (step 404) relating to the received waves. Using the received data, the controller determines a characteristic of the target (step 406) and engages the second scanning mode (step 408) to conduct a second scan of the target. The controller utilizes the characteristic determined in step 406 to determine a parameter of the second scanning mode to, by way of example, reduce the risk that the target may receive an inappropriate dose. The detector again receives waves (step 410) and the data is then analyzed the data (step 412).

According to one embodiment, the controller produces a representation (i.e. a scan, an image, a profile, a schematic) that may be presented to the operator (step 414). Based on the representation and a module having instructions for determining whether the representation includes contraband, the controller may determine whether a danger (i.e. the presence of contraband) exists (step 416). Where a danger exists, the controller may send a signal (step 418) to identify the contraband, indicate to the operator that contraband may be present (e.g., with an indicator), or may provide an indication of the contraband on a display for the operator's review. Where no contraband is detected, the controller may indicate that the target is clear (step 419). The controller may alternatively indicate the presence of contraband (step 418) without indicating the absence of contraband.

Referring to FIG. 8, a controller is configured to operate a detector according to another method. The controller engages the first scanning mode (step 450), receives data (step 452), and the data is analyzed to produce a representation of the target (step 454). The controller evaluates the representation (step 456) and determines whether the quality (i.e. resolution, etc.) of the representation is above a threshold value (i.e. a value sufficient for the controller to determine whether the target possesses contraband). Where the representation is of sufficient quality, the controller determines whether the representation indicates the presence of contraband (step 458). The controller indicates the presence of contraband (step 460) or the absence of contraband (step 462). Where the quality of the representation is not above a threshold level, the controller engages the second scanning mode (step 464), receives data in step 466, and the data is analyzed (step 468) to produce a representation (step 470). The controller determines whether the representation indicates the presence of contraband (step 472). The controller indicates the presence of contraband (step 474) or the absence of contraband (step 478). The controller may alternatively indicate the presence of contraband (step 474) without indicating the absence of contraband. According to another embodiment, the controller iteratively evaluates the quality of the representation and performs additional scans until the quality of the representation reaches the threshold level. According to still another embodiment, the controller both determines the quality of the representation and determines a characteristic of the target to, by way of example, improve the accuracy of the detector while reducing the likelihood that a target may receive an inappropriate dose.

Figure 9:
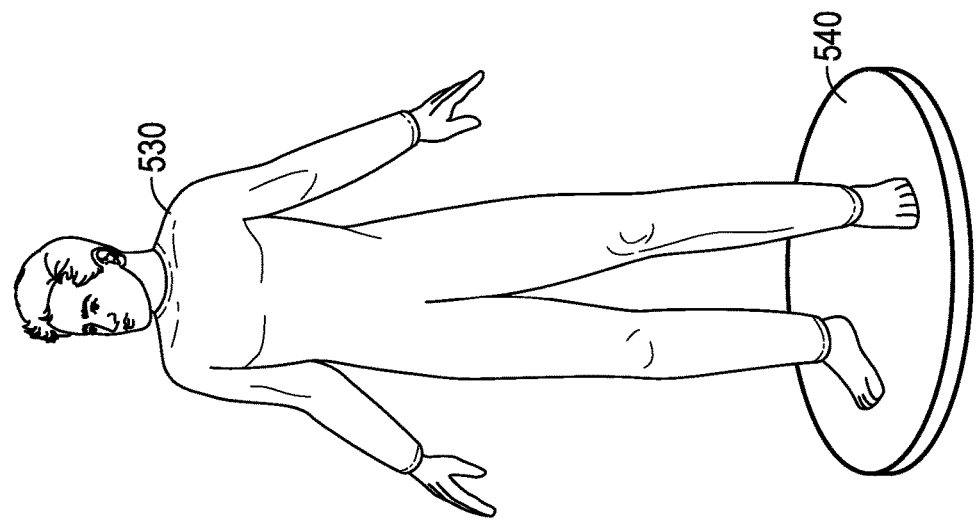
FIG. 9 is a schematic view of a detection device including a measuring device, according to one embodiment.
Figure 9:
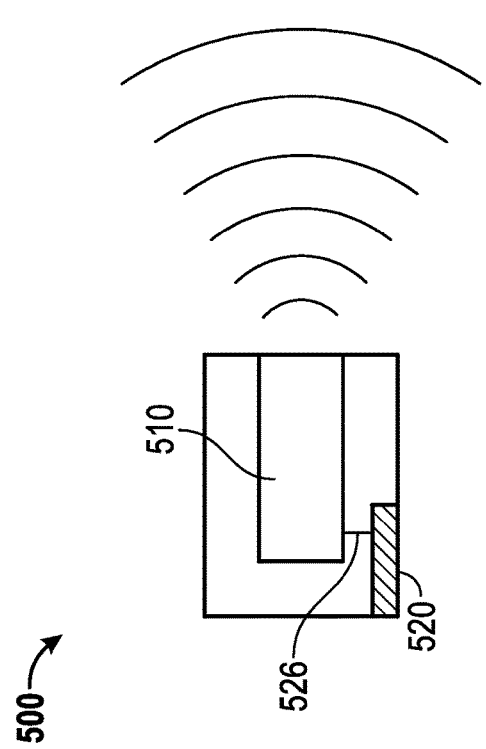

Referring next to the embodiments shown in FIGS. 9-10, a detector, shown as detector 500, includes a scanner, shown as scanner 510. A controller, shown as controller 520 is coupled to scanner 510 with a data link, shown as cable 525. As discussed above, the detector may be configured to direct waves toward a target, shown as person 530. According to one embodiment, detector 500 includes a measuring device, shown as scale 540. In some embodiments, scale 540 may facilitate the use of a characteristic (e.g., weight) of person 530 as part of a contraband detection scheme. As shown in FIG. 9, person 530 may be directed onto scale 540. According to one embodiment, scale 540 is configured to produce a weight signal to controller 520 of detector 500. According to another embodiment, the scale 540 may indicate the weight of person 530 to an operator, who may enter the weight into an operator interface. As discussed above, controller 520 may utilize the weight of person 530 to determine (e.g. based on data, with algorithms, etc.) a feature of person 530 (e.g., the thickness of fatty tissue). Including a feature as part of the contraband detection scheme may reduce the likelihood that person 530 may receive an inappropriate dose from detector 500.

According to the embodiment shown in FIG. 10, detector 500 includes a measuring device, shown as height indicator 550. In some embodiments, height indicator 550 may facilitate the use of a characteristic (e.g., height) of person 530 as part of a contraband detection scheme. As shown in FIG. 10, person 530 may be directed to stand near height indicator 550. According to one embodiment, height indicator 550 is configured to produce a height signal (e.g., using a plurality of proximity sensors, a laser measurement system, a camera, etc.) and provide the height signal to controller 520 of detector 500. According to another embodiment, the height indicator 550 may indicate the height of person 530 to an operator, who may enter the height into an operator interface. As discussed above, controller 520 may utilize the height of person 530 to determine (e.g. based on data, with algorithms, etc.) a feature of person 530 (e.g., the thickness of fatty tissue, a body mass index, etc.). Including a feature as part of the contraband detection scheme may reduce the likelihood that person 530 may receive an inappropriate dose from detector 500. According to still another embodiment, detector 500 may include a scale and a height indicator or still other systems to determine a characteristic of person 530.

In some embodiments, detector 500 includes an imaging measurement device (e.g., a visible wavelength camera, a non-visible wavelength camera, a multi-spectral camera, etc.). The imaging measurement device may provide one or more still images or may provide video imagery. The imaging measurement device may produce three-dimensional image information (e.g., by using stereoscopic imaging, by using range data combined with a conventional camera, by determining range from image focal quality, etc.). In other embodiments, a processor is configured to produce three-dimensional image information using image information received from the imaging measurement device. According to one embodiment, the imaging measurement device uses ultrasound or radio frequency radiation. The imaging measuring device may use techniques such as radiofrequency thermometry or IR radiation to determine a thermal image of the person.

An image recognition system (e.g., implemented in software or in hardware) may utilize the image information from the imaging measurement device to automatically determine characteristics of the target (e.g., height, gender, pregnancy status, body structure, etc.). The image recognition system may be used in conjunction with population-wide correlations, machine-learning algorithms, or still other systems to estimate characteristics such as age, weight, physiological stress, medical condition, or still other features of the target. In some embodiments, the image recognition system includes a facial recognition system. The facial recognition system may utilize a database (e.g., a global database, a situation-specific database, etc.) to determine an identity of the target. The identity of the target may be used to retrieve other characteristics of the person from an information database.

According to one embodiment, the methods, and contraband detection schemes described herein are implemented as part of a security-scanning device. By way of example, the security-scanning device may include the ProVision® ATD or the ProVision® 2 body scanners manufactured by L-3 Communications. In another example, the security-scanning device may include the Rapiscan Secure 1000 SP or the Rapiscan Secure 1000 DP body scanners manufactured by Rapiscan Systems. The scanners or other components disclosed herein may be implemented into these or other security scanning devices.

It is important to note that the construction and arrangement of the elements of the systems and methods as shown in the embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. The order or sequence of any process or method steps may be varied or re-sequenced according to other embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other embodiments without departing from scope of the present disclosure or from the spirit of the appended claims.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data, which cause a general-purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

What is claimed is:

1. A method, comprising:
    engaging a scanner in a first scanning mode that includes a first scanning of a standing individual with a first scanning beam of electromagnetic waves;
    receiving a return of the first scanning beam of electromagnetic waves from the standing individual;
    producing a representation of the standing individual based on the returned first scanning beam of electromagnetic waves;
    determining a property of a second scanning mode based on the representation;
    engaging the scanner in the second scanning mode that includes a second scanning of the standing individual with a second scanning beam of electromagnetic waves;
        receiving a return of the second scanning beam of electromagnetic waves from the standing individual;
        determining a threat that the standing individual carries contraband based upon the returned second scanning beam of electromagnetic waves; and
        outputting a human-perceivable notification of the determined threat.

2. The method of claim 1, further comprising determining a maximum allowable dosage for the individual based on a characteristic of the individual and a maximum dose exposure limit for the individual.

3. The method of claim 1, further comprising determining an allowable dosage with the controller based on a characteristic of the individual.

4. The method of claim 1, further comprising determining a maximum allowable dosage for the individual based on a characteristic of the individual.

5. The method of claim 1, wherein the property includes a dose that may be received by the individual.

6. The method of claim 5, wherein the dose that may be received by the individual during the second scanning mode is greater than the dose that may be received by the individual during the first scanning mode.

7. The method of claim 1, wherein the property includes a target area of the individual.

8. The method of claim 7, wherein the target area of the individual corresponds to a portion of the initial representation having an image quality that is at least one of less than other portions of the initial representation and below a threshold level.

9. The method of claim 7, wherein the target area of the individual corresponds to a portion of the initial representation potentially indicating a suspect object.

10. The method of claim 1, further comprising determining a characteristic of the individual with the controller using the initial scan.

11. The method of claim 10, wherein the characteristic includes at least one of age, gender, weight, a medical condition, and body structure.

12. The method of claim 10, wherein the characteristic includes a pregnancy status.

13. The method of claim 1, wherein the first scanning mode comprises a physiological scan.

14. The method of claim 13, further comprising determining at least one of a body temperature of the individual and a stress level of the individual with the physiological scan.

15. The method of claim 1, wherein the first scanning mode comprises at least one of an optical scan, a biometric identification scan, and an infrared scan.

16. The method of claim 1, wherein the first scanning mode comprises at least one of a microwave scan, an ultrasound scan, and a radiofrequency scan.

17. The method of claim 1, wherein the first scanning mode comprises at least one of a backscattering x-ray scan and a transmissive x-ray scan.

18. The method of claim 1, wherein the standing individual includes a standing individual entering a secured area.

19. The method of claim 1, wherein the standing individual includes a free-standing individual.

20. The method of claim 1, wherein the standing individual includes an unsupported individual.

21. A security device, comprising:
    a scanner configured to transmit at least two selectable scanning beams of electromagnetic waves at a standing individual, and to receive returned electromagnetic waves from the standing individual;
    a controller configured to:
        engage the scanner in a first scanning mode that includes a first scanning of the standing individual with a first scanning beam of electromagnetic waves;
        receive a return of the first scanning beam of electromagnetic waves from the standing individual;
        produce a representation of the standing individual based on the returned first scanning beam of electromagnetic waves;
        determine a property of a second scanning mode based on the representation;
        engage the scanner in a second scanning mode that includes a second scanning of the standing individual with a second scanning beam of electromagnetic waves;
        receive a return of the second scanning beam of electromagnetic waves from the standing individual; and
        determine a threat that the standing individual possesses contraband based upon the returned second scanning beam of electromagnetic waves; and
    an indicator device configured to output a human-perceivable alert of the determined threat.

22. The security device of claim 21, wherein the controller is configured to determine a maximum allowable dosage for the individual based on a characteristic of the individual and a maximum dose exposure limit for the individual.

23. The security device of claim 21, wherein the controller is configured to determine an allowable dosage with the controller based on a characteristic of the individual.

24. The security device of claim 21, wherein the controller is configured to determine a maximum allowable dosage for the individual based on a characteristic of the individual.

25. The security device of claim 21, wherein the property includes a dose that may be received by the individual.

26. The security device of claim 25, wherein the dose that may be received by the individual during the second scanning mode is greater than the dose that may be received by the individual during the first scanning mode.

27. The security device of claim 21, wherein the property includes a target area of the individual.

28. The security device of claim 27, wherein the target area of the individual corresponds to a portion of the initial representation having an image quality that is at least one of less than other portions of the initial representation and below a threshold level.

29. The security device of claim 27, wherein the target area of the individual corresponds to a portion of the initial representation potentially indicating a suspect object.

30. The security device of claim 21, wherein the controller is configured to determine a characteristic of the individual with the controller using the initial scan.

31. The security device of claim 30, wherein the characteristic includes at least one of age, gender, weight, a medical condition, and body structure.

32. The security device of claim 30, wherein the characteristic includes a pregnancy status.

33. The security device of claim 21, wherein the first scanning mode comprises a physiological scan.

34. The security device of claim 33, wherein the controller is configured to determine at least one of a body temperature of the individual and a stress level of the individual with the physiological scan.

35. The security device of claim 21, wherein the first scanning mode comprises at least one of an optical scan, a biometric identification scan, and an infrared scan.

36. The security device of claim 21, wherein the first scanning mode comprises at least one of a microwave scan, an ultrasound scan, and a radiofrequency scan.

37. The security device of claim 21, wherein the first scanning mode comprises at least one of a backscattering x-ray scan and a transmissive x-ray scan.

38. The security device of claim 21, wherein the standing individual includes a free-standing individual.

39. The security device of claim 21, wherein the standing individual includes an unsupported standing individual.

* * * * *